US011453854B2

(12) United States Patent
Daoussi et al.

(10) Patent No.: US 11,453,854 B2
(45) Date of Patent: Sep. 27, 2022

(54) LYOPHILIZATION METHODS THAT PROVIDE STABLY DEHYDRATED PROTOZOANS FOR USE AS POTENT LIVE VACCINES

(71) Applicant: Zoetis Services LLC, Parsippany, NJ (US)

(72) Inventors: Rim Daoussi, Louvain-la-Neuve (BE); Frederick H. Weber, Mattawan, MI (US)

(73) Assignee: Zoetis Services LLC, Parsippany, NJ (US)

( * ) Notice: Subject to any disclaimer, the term of this patent is extended or adjusted under 35 U.S.C. 154(b) by 16 days.

(21) Appl. No.: 16/338,726

(22) PCT Filed: Oct. 4, 2017

(86) PCT No.: PCT/US2017/055056
§ 371 (c)(1),
(2) Date: Apr. 2, 2019

(87) PCT Pub. No.: WO2018/067647
PCT Pub. Date: Apr. 12, 2018

(65) Prior Publication Data
US 2021/0284950 A1  Sep. 16, 2021

Related U.S. Application Data

(60) Provisional application No. 62/404,448, filed on Oct. 5, 2016.

(51) Int. Cl.
*C12N 1/04* (2006.01)
*A61K 9/16* (2006.01)
*A61K 9/19* (2006.01)
*A61K 39/002* (2006.01)
*A61K 39/00* (2006.01)

(52) U.S. Cl.
CPC .............. *C12N 1/04* (2013.01); *A61K 9/1617* (2013.01); *A61K 9/1623* (2013.01); *A61K 9/1658* (2013.01); *A61K 9/19* (2013.01); *A61K 39/002* (2013.01); *A61K 2039/521* (2013.01); *A61K 2039/522* (2013.01)

(58) Field of Classification Search
None
See application file for complete search history.

(56) References Cited

U.S. PATENT DOCUMENTS

| | | |
|---|---|---|
| 3,783,098 A | 1/1974 | Calnek et al. |
| 3,915,794 A | 10/1975 | Zygraich et al. |
| 4,000,256 A | 12/1976 | Hilleman et al. |
| 5,078,996 A | 1/1992 | Conlon, III et al. |
| 5,707,617 A | 1/1998 | Conrad et al. |
| 5,723,127 A | 3/1998 | Scott et al. |
| 5,856,172 A | 1/1999 | Greenwood et al. |
| 5,964,043 A * | 10/1999 | Oughton ............... F26B 5/06 34/92 |
| 6,656,479 B2 | 12/2003 | Brake et al. |
| 6,787,146 B2 | 9/2004 | Brake et al. |
| 7,361,359 B2 | 4/2008 | Ellis et al. |
| 7,462,359 B2 * | 12/2008 | Choromanski ......... A61P 33/02 424/269.1 |
| 2004/0131633 A1 | 7/2004 | Ellis et al. |
| 2010/0255577 A1 | 10/2010 | Ortega Mora et al. |

FOREIGN PATENT DOCUMENTS

| | | |
|---|---|---|
| CA | 2640590 C | 8/2007 |
| CN | 102511471 A | 6/2012 |
| CN | 103299986 A | 9/2013 |
| EA | 011578 B1 | 4/2009 |
| EP | 0145197 A2 | 6/1985 |
| JP | 60-176580 A2 | 9/1985 |
| JP | 2003-505482 T2 | 2/2003 |
| JP | 2007-519712 T2 | 7/2007 |
| JP | 2012-500021 T2 | 1/2012 |
| JP | 2016-65098 A2 | 4/2016 |
| RU | 2481825 C2 | 5/2013 |
| WO | WO 2015/175672 A1 | 11/2015 |
| WO | WO-2015175672 A1 * | 11/2015 ........... A61K 9/0019 |

OTHER PUBLICATIONS

Geidobler et al. 2012 (A New Approach to Achieve Controlled Ice Nucleation of Super-cooled Solutions During the Freezing Step in Freeze-Drying; Journal of Pharmaceutical Sciences 101 (12): 4409-4413). (Year: 2012).*
Pusterla, N. et al., 2011, "Endogenous Transplacental Transmission of Neospora hughesi in Naturally Infected Horses", Journal of Parasitology, vol. 97, pp. 281-285.
Dubey, J.P., 1999, "Neosporosis—the first decade of research", International Journal for Parasitology, vol. 29, pp. 1485-1488.
Dubey, J.P. et al., 2002, "Neospora caninum and Hammondia heydorni are separate species", Trends in Parasitology, vol. 18, pp. 66-69.
McAllister, M.M. et al., 1998, Rapid Communication Dogs are definitive hosts of Neospora caninum, International Journal for Parasitology, vol. 28, pp. 1473-1478.
Belli, S.I. et al., 2006, "The coccidian oocyst: a tough nut to crack!", Trends in Parasitology, vol. 22, pp. 416-423.
Mai, K. et al., 2009, "Oocyst wall formation and composition in coccidian parasites", Mem. Inst. Oswaldo Cruz, Rio de Janeiro, vol. 104, pp. 281-289.
Goodswen, S.J. et al., 2013, "A review of the infection, genetics, and evolution of Neospora caninum: From the past to the present", Infection, Genetics and Evolution, vol. 13, pp. 133-150.
Mille, Y. et al., 2003, "Magnitude and Kinetics of Rehydration Influence the Viability of Dehydrated E. coli K-12", Biotechnology and Bioengineering, vol. 83, pp. 578-582.
Weber, F.H. et al., 2013, "On the Efficacy and Safety of Vaccination with Live Tachyzoites of Neospora caninum for Prevention of Neospora-Associated Fetal Loss in Cattle", Clinical and Vaccine Immunology, vol. 20, pp. 99-105.

(Continued)

*Primary Examiner* — Mary Maille Lyons
(74) *Attorney, Agent, or Firm* — Scott C. Mayhew

(57) ABSTRACT

An improved stabilization buffer for use in the lyophilization of *Neospora* and other protozoans is disclosed. Also disclosed is an improved lyophilization method, which includes controlling ice nucleation during the freezing step.

19 Claims, No Drawings

(56) References Cited

OTHER PUBLICATIONS

Remington: The Science and Practice of Pharmacy, 20th ed, Lippincott Williams & Wilkins, pub., 2000.
The Handbook of Pharmaceutical, Excipients, 4.sup.th edit., eds. R. C. Rowe et ai, APhA Publications, 2003.
Flosdorf, E.W. et al., 1935, "Procedure and Apparatus for Preservation in "Lyophile" Form of Serum and Other Biological Substances", Journal of Immunology, vol. 29, pp. 389-425.
Stamp, L., 1947, "The Preservation of Bacteria by Drying", Journal of General Microbiology, vol. 1, pp. 251-265.
Rightsel, W.A. et al, 1967, "Freezing and Freeze-Drying of Viruses", Cryobiology, vol. 3, pp. 423-431.
Rowe, A.W. et al., 1971, "Effect of glycerol, HES, and DMSO on functional integrity of human blood platelets before and after freezing", Cryobiology, vol. 8, p. 397.
Bovarnick, M.R. et al., 1950, "The influence of certain salts, amino acids, sugars, and proteins on the stability of rickettsiae", Journal of Bacteriology, vol. 59, pp. 509-522.
Wang, W., 2000, "Lyophilization and development of solid protein pharmaceuticals", International Journal of Pharmaceutics, vol. 203, pp. 1-60.
Carpenter, J.F., 1997, "Rational Design of Stable Lyophilized Protein Formulations: Some Practical Advice", Pharmaceutical Research, vol. 14, pp. 969-975.
Miyake, Y. et al., 2004, "Cryopreservation of protozoan parasites", Cryobiology, vol. 48, pp. 1-7.
Morris, G.J. et al., 2013, "Controlled ice nucleation in cryopreservation—A review", Cryobiology, vol. 66, pp. 85-92.
PCT International Application No. PCT/US2017/055056, PCT Search Report and Written Opinion, International Filing Date Oct. 4, 2017.
Japanese Patent Office, Japanese Patent Application No. 2019-518210, First Office Action Non-English, Filing Date Aug. 22, 2019, Drafting Date Jul. 2, 2021.
Japanese Patent Office, Japanese Patent Application No. 2019-518210, First Office Action English Translation, Filing Date Aug. 22, 2019, Drafting Date Jul. 2, 2021.
China National Intellectual Property Administration, China Patent Application No. 201780061660.2, First Office Action and Search Report Non-English, Filing Date Oct. 4, 2017, dated Nov. 27, 2020.
China National Intellectual Property Administration, China Patent Application No. 201780061660.2, First Office Action and Search Report English Translation, Filing Date Oct. 4, 2017, dated Nov. 27, 2020.
Patent Office of the Russian Federation, Russian Patent Application 2019107886/04(015218), Office Action Non-English, Filing Date Oct. 4, 2017, Date of Correspondence Receipt Nov. 13, 2019.
Patent Office of the Russian Federation, Russian Patent Application 2019107886/04(015218), Office Action English Translation, Filing Date Oct. 4, 2017, Date of Correspondence Receipt Nov. 13, 2019.
Patent Office of the Russian Federation, Russian Patent Application 2019107886/04(015218), Search Report Non-English, Filing Date Oct. 4, 2017, Date of Actual Completion of the Search: Nov. 12, 2019.
Patent Office of the Russian Federation, Russian Patent Application 2019107886/04(015218), Search Report English Translation, Filing Date Oct. 4, 2017, Date of Actual Completion of the Search: Nov. 12, 2019.
European Patent Convention, EP Patent Application 17798019.0, Annex to Communication dated Jul. 28, 2020.
Canada Patent Office, Canada Patent Application No. 3,037,544, Date of Communication Nov. 5, 2020.

* cited by examiner

LYOPHILIZATION METHODS THAT PROVIDE STABLY DEHYDRATED PROTOZOANS FOR USE AS POTENT LIVE VACCINES

The present application is the U.S. national stage (37 USC 371) of international application PCT/US2017/055056, internationally filed Oct. 4, 2017, and claims the benefit of U.S. Provisional Application 62/404,448 flied Oct. 5, 2016. The complete disclosures of the PCT/US2017/055056 international application and the 62/404,448 U.S. provisional application are incorporated by reference herein, as if fully set forth.

FIELD OF THE INVENTION

The present invention relates particularly to methods of lyophilizing and preserving the viability of *Neospora caninum*. The invention is also applicable to improved preservation (stabilization) processes for maintaining the viability, immunogenicity and infectivity of lyophilized protozoa generally.

BACKGROUND OF THE INVENTION

*Neospora caninum* is an obligate, intracellular, coccidian, protozoan parasite. The taxonomic classification of *Neospora* is as follows: Phylum-Apicomplexa; Class-Coccidia; Order-Eucoccidiorida; Family-Sarcocystidae; Genus-*Neospora*. The phylum, Apicomplexa, contains several clearly defined groups, based on phenotypic characteristics including: coccidians (*Neospora; Toxoplasma; Hammondia, Cryptosporidium*); gregarines (e.g. *Lankesteria*), and haemospridians (e.g. *Plasmodiu*; piroplasms (e.g. *Theileria*).

*N. caninum* is capable of infecting domestic and wild canids, as well as ruminants. In canines, neosporosis manifests as a neuromuscular disease. In Norway in the mid-1980's, *N. caninum* infection in dogs caused widely reported cases of neuromuscular degeneration, which led to hind limb paralysis. Neosporosis, in both beef and dairy cattle, is an economically costly disease, and is the most commonly diagnosed cause of bovine abortion. Another *Neospora* species-*Neospora hughesican* infect horses, and is associated with fetal myeloencephalitis (Pusterla et al., J. Parasitol., 97:281-5; 2011).

Prior to 1988, *N. caninum* was misclassified as *Toxoplama gondii*, due to structural similarities between the two (Dubey, Int J Parasitol. 29(10):1485-8; 1999). Both species are tissue-dwelling coccidians, and share many common biological and morphological features. Even the initial recognition of *N. caninum* as a species, however, was questioned, due to the extreme similarities that it shares with *Hammondia heydorni* (Dubey et al., Trends Parasitol., 18:66-9; 2002). While there are genetic differences between the two organisms, they are physically very similar; and oocysts of *H. heydorni* are morphologically indistinguishable from those of *N. caninum* (McAllister et al, J Parasitol., 28:1473-9; 1998).

The life cycle of *Neospora caninium* includes both sexual replication in a canid (definitive) host, and asexual replication in an intermediate host such as a bovine. Oocysts passed in the feces of the definitive host may be ingested by cattle, after which motile tachyzoites are released which in turn spread throughout the tissues of the infected bovine. The tachyzoites in turn develop into bradyzoite forms, which form cysts in muscle. Canids become infected by eating contaminated meat, and shed oocysts in their own feces.

Oocysts are essentially thick-walled spores, and their robust wall, consisting mainly of protein (67-90%), allows them to survive for long periods of time outside of a host. The oocyst wall, while resistant to mechanical and chemical damage, however, is susceptible to the effects of freezing and thawing. In part, this is due to the detrimental effects of expansion and contraction of the rigid oocyst wall that occur during freezing and thawing. Tachyzoites, however, are rapidly-dividing, motile, and more fluid in their membrane structure than oocysts. (Belli et al., Trends Parasitol., 22(9):416-23, 2006; Mai et al., Mem. Inst. Oswaldo Cruz, 104(2):281-9, 2009; Goodswen et al., Infection, Genetics, Evolution, 13:133-50, 2013). Even with tachyzoites, however, damaging effects can occur due to the formation of intracellular and extracellular ice crystals. This must be minimized and controlled, particularly during the lyophilization process. The lyophilization and stabilization procedures of the present invention are generally applicable to all life cycle phases of Apicomplexa protozoans.

Lyophilization (freeze-drying) is a commonly-used technique to remove water in the preparation of dehydrated products. Generally, lyophilization involves three steps: (1) an aqueous composition is frozen at a low temperature; (2) the majority of the water is removed by sublimation under conditions of reduced pressure and low temperature; and (3) remaining bonded water is further removed by desorption under conditions of reduced pressure and higher temperatures. The freeze-dried product contains very low residual water (from about 0.5-5.0% w/w), and the dry material is in an amorphous form. Prior to use, the dried products must be rehydrated. Damage to the freeze-dried products, including loss of viability, diminished immunogenicity, and impaired/abolished infectivity, can occur during any of the above-recited steps. Accordingly, stabilizing ingredients (cryoprotectants/lyoprotectants) and buffers are often added to compositions prior to subjecting them to lyophilization, and the magnitude and kinetics of each step, particularly the rehydration step, must be precisely defined (Mille et al., Biotech Bioeng. 83, 578; 2003).

Immunogenic compositions comprising biological ingredients, including protozoa such as *Neospora*, are markedly sensitive to the conditions by which they are prepared, formulated and stored. In a study in which cattle were immunized with *N. caninum* tachyzoites, it was demonstrated that protection was decreased if the tachyzoites were frozen at −80 C in DMSO, versus ones which were not frozen (Weber et al.; Clin Vaccine Immunol., 20(1):99-105, 2013). While a large number of compounds have been tested for their ability to stabilize different compositions containing live attenuated biological ingredients, there still remains a need for new preservation solutions, as well as improved freeze-drying processes, for preserving the viability, immunogenicity and infectivity of protozoa, including *Neospora*, and all aforementioned *Apicomlexa.*

SUMMARY OF THE INVENTION

The applicants have surprisingly identified, and disclosed herein, more effective stabilizing formulations, as well as improved methods for lyophilizing protozoa, including *Neospora.*

One embodiment of the invention provides a method of lyophilizing a protozoan, wherein said method comprises the use of a stabilizing buffer comprising a component selected from the group consisting of bovine serum albumin, polysorbate 80, and fetal bovine serum.

Another embodiment provides that the buffer of the previous embodiment comprises bovine serum albumin, polysorbate 80, and fetal bovine serum.

Another embodiment provides that the buffer of the previous embodiments further comprises: trehalose; citric acid; and epigallocatechin gallate (EGCG) which can also be replaced with ascorbic acid (for all embodiments of the invention).

A further embodiment provides a method of lyophilizing a protozoan, wherein said method comprises, during the freezing step, controlling ice nucleation by pressurizing and depressurizing with an inert gas or air.

Another embodiment provides that during the method of the previous embodiment, ice nucleation is controlled by pressurizing and depressurizing with an inert gas.

Another embodiment provides that the inert gas is nitrogen or argon.

A further embodiment provides that the method of lyophilization comprises the steps of:

A. Loading a mixture of cells, protozoa, and a stabilizing buffer into a dryer chamber which is at approximately 5° C. and about 1 Bar;

B. Lowering the temperature of the chamber to between −1° C. and −15° C., and holding for approximately 5 minutes;

C. Pressurizing the chamber to between 1.2 to 2 Bar, and holding for approximately 45 minutes, while maintaining the temperature of the chamber at between −1° C. and −15° C.;

D. Rapidly depressurizing the chamber to about 1 Bar, while holding the temperature at between −1° C. and −15° C.;

E. Holding the pressure in the chamber at about 1 Bar, lowering the temperature to as low as −50° C., and holding for approximately 45 minutes;

F. Holding the pressure in the chamber at about 1 Bar, the temperature at as low as −50° C., for a further approximate 90 minutes; G. Holding the temperature in the chamber at as low as −50° C., decreasing the chamber pressure to about 0.1 mBar, and holding for approximately 30 minutes;

H. Holding the temperature in the chamber at as low as −50° C., decreasing the chamber pressure to about 0.01 mBar, and holding for approximately 60 minutes;

I. Holding the pressure in the chamber at about 0.01 mBar, raising the temperature in the chamber to as high as −35° C., and holding for approximately 60 minutes;

J. Holding the pressure in the chamber at about 0.01 mBar, and the temperature at as high as −35° C., and holding for up to an additional 3500 minutes;

K. Decreasing the chamber pressure to about 0.005 mBar; raising the temperature to as high as 20° C., and holding for up to an additional 360 minutes;

L. Holding the pressure in the chamber at about 0.005 mBar; and the temperature at as high as 20° C., for up to an additional 900 minutes.

Another embodiment provides that the protozoan is from the phylum Apicomplexa.

An additional embodiment provides that the protozoan is selected from the class Coccidia.

An additional embodiment provides that the protozoan is selected from the order Eucoccidiorida.

An additional embodiment provides that the protozoan is selected from the family Sarcocystidae.

An additional embodiment provides that the protozoan is selected from the genus consisting of *Neospora*, *Hammondia*, and *Toxoplasma*.

An additional embodiment provides that the protozoan is from the genus *Neospora*.

An additional embodiment provides that the protozoan is *Neospora caninum*.

A further embodiment provides that the method of a previous embodiment is the final step in the preparation of a vaccine.

A further embodiment provides that the method of a previous embodiment is an intermediate step in the preparation of a vaccine.

A further embodiment provides that *Neospora caninum* is inactivated.

A further embodiment provides that *Neospora caninum* is live-attenuated.

A further embodiment provides that *Neospora caninum* is selected from the group consisting of: Nc-Spain 7, NCTS-8, Nc-Nowra, NC-1, and NE1.

A further embodiment provides that live-attenuated *Neospora caninum* has a mutation in a protein selected from the group consisting of: PTS, MIC-1, MIC-3, IMP-1, GRA1, GRA6, GRA7, AMA1, SAG1, SAG4, GRA2, sortilin-like receptor, CPS II, RON2, digalactolipid antigen; CyP; NcP20, and DHFR.

An additional embodiment provides that *Neospora caninum* is lyophilized by the method of a previously disclosed embodiment.

A further embodiment provides that the *Neospora caninum* vaccine is prepared by a process comprising the method of a previously disclosed embodiment.

DETAILED DESCRIPTION OF THE INVENTION

All publications, patent applications, patents, and other references mentioned herein are incorporated by reference in their entirety.

The following definitions may be applied to terms employed in the description of the embodiments. The following definitions supersede any contradictory definitions contained in each individual reference incorporated herein by reference.

Unless otherwise defined herein, scientific and technical terms used in connection with the present embodiments shall have the meanings that are commonly understood by those of ordinary skill in the art. Further, unless otherwise required by context, singular terms shall include pluralities, and plural terms shall include the singular.

The terms, "comprises," "comprising," "containing" and "having" and the like, as used herein, can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "adjuvant", as used herein, means a pharmacological or immunological agent that modifies the effect of other agents, such as a drug or immunogenic composition. Adjuvants are often included in immunogenic compositions to enhance the recipient's immune response to a supplied antigen.

The term "antigen", as used herein, means a substance that is recognized by the immune system and induces an immune response. The antigen may comprise a whole organism, killed, attenuated or live; a subunit or portion of an organism; a recombinant vector containing an insert with immunogenic properties; a nucleic acid piece or fragment capable of inducing an immune response upon presentation to a host animal; a protein, a polypeptide, a peptide, a glycoprotein, a hapten, a carbohydrate, a sugar, or any combination thereof. Alternatively, the antigen may comprise a toxin or antitoxin. A similar term used interchangeably in this context is "immunogen".

The term "attenuated", as used herein, refers to a strain of a microorganism whose pathogenicity has been reduced so that it will initiate an immune response without producing the specific disease. An attenuated strain is less virulent than the parental strain from which it was derived. Attenuated microorganisms can be screened in vitro or in vivo to confirm that they are less pathogenic than its parental strain. Conventional means are used to introduce attenuating mutations, such as in vitro passaging, as well as chemical mutagenesis. An alternative means of attenuating comprises making pre-determined mutations using site-directed mutagenesis, where one or more mutations may be introduced. The term "more attenuated", as used herein, refers to a strain which has been further modified beyond the attenuated strain from which it was derived. This further attenuation can be achieved through additional in vitro passaging, or additional rounds of chemical or site-directed mutagenesis.

The term "ice nucleation", as used herein, means the onset of freezing, or the conversion of water droplets to ice.

The term "immunogenic composition" or "immunizing amount", as used herein, means a composition that generates an immune response (i.e., has immunogenic activity) when administered alone, or with a pharmaceutically-acceptable carrier, to an animal. The immune response can be a cellular immune response mediated primarily by cytotoxic T-cells, or a humoral immune response mediated primarily by helper T-cells, which in turn activate B-cells, leading to antibody production. In addition, specific T-lymphocytes or antibodies can be generated to allow for the future protection of an immunized host.

The term "inert gas", as used herein, means a gas which does not undergo chemical reactions under a set of given conditions. Nitrogen can be used as an inert gas; noble gases can also be used as inert gases, including argon.

The term "isolated", as used herein, means that the referenced material is removed from the environment in which it is normally found. Thus, an isolated biological material can be free of cellular components, i.e., components of the cells in which the material is found or produced. An isolated material may be, but need not be, purified.

The terms "lyophilize" or "lyophilization", as used herein, mean a process consisting of two main stages: freezing (solidification), and drying, the latter of which can be subdivided into two phases-primary drying (ice sublimation) and secondary drying (moisture desorption).

The term "parasite", as used herein, means an organism that lives in or on an organism of another species. Some parasites only replicate within a host organism (obligate intracellular), but others can multiply freely in the environment (facultative intracellular). Parasites can consist of one cell, as in the case of Giardia, or many cells, as with parasitic worms.

The term "pathogen", as used herein, means a specific causative agent of disease, such as a bacterium, fungus, protozoan, or virus.

The terms "prevent", "preventing" or "prevention", and the like, as used herein, mean to inhibit the replication of a microorganism, to inhibit transmission of a microorganism, or to inhibit a microorganism from establishing itself in its host. These terms, and the like, can also mean to inhibit or block one or more signs or symptoms of infection.

The term "protozoa" or "protozoan", as used herein, means a diverse group of unicellular eukaryotic organisms. The terms are also used informally to designate single-celled, non-photosynthetic protists, such as ciliates, amoebae and flagellates. Historically, protozoa were defined as single-celled organisms with animal-like behaviors, such as motility and predation. *Neospora* is an important protozoan pathogen, and has a life cycle similar to *Toxoplasma*.

The term "stabilizer", as used herein, means a compound or formulation which, when added to a pharmaceutical product, prevents or reduces physical and/or chemical degradation when the product is stored. With respect to lyophilization, stabilizers can prevent or reduce the damage to labile products (e.g. microorganisms) caused by ice nucleation during the freezing process.

The term "subject", as used herein, means a vertebrate, such as a mammal, bird, reptile, amphibian or fish; more advantageously a human, a companion or domesticated animal; a food-producing or feed-producing animal; livestock, game, racing or sport animal such as, but not limited to, bovines, canines, felines, caprines, ovines, porcines, equines, and avians. Preferably, the vertebrate is a bovine or a canine.

The term "tachyzoite", as used herein, means a rapidly-multiplying stage in the development of the tissue phase of certain coccidia, including *Neospora* and *Toxoplasma*. Tachyzoites are motile, and divide by endodyogeny and endopolygeny, in contrast to bradyzoites, which are sessile and slow-growing.

The terms "vaccine" and "vaccine composition", as used herein, mean any composition that induces a protective immune response against the antigen of interest, and/or which efficaciously protects against the antigen.

The following description is provided to aid those skilled in the art in practicing the present invention. Even so, this description should not be construed to unduly limit the present invention, as modifications and variations in the embodiments discussed herein can be made by those of ordinary skill in the art, without departing from the spirit or scope of the present inventive discovery.

Immunogenic Compositions

The active immunogenic component can be a protozoan. The protozoan may comprise, but not be limited to, *Neospora* species (e.g. *Neospora caninum; Neospora hughesi*), *Toxoplasma* species (e.g. *Toxoplasma gondii*), Hammondia species (e.g. *Hammondia heydorni*), Besnoitia species, *Cystoisospora* species, *Frenkelia* species, *Nephroisospora* species, *Sarcocystis* species, and *Hyaloklossia* species. Other protozoa that may be manipulated according to the practice of the invention in order to provide immunogenic compositions include *Theileria* species, *Plasmodium* species, *Trypanosome* species, *Giardia* species, *Boophilus* species, *Babesia* species, *Entamoeba* species, *Eimeria* species, *Leishmania* species, *Schistosoma* species, *Brugia* species, Fascida species, *Dirofilaria* species, *Wuchereria* species, *Onchocerea* species, *Treponema* species, *Cryptococcus* species, *Coccidia* species, *Histomoniasis* species, *Hexamitiasis* species, and all *Cryptosporidium* species such as *C. parvum* and *C. hominus*.

The *Neospora caninum* isolate may be attenuated or inactivated. Attenuated *N. caninum* isolates can be selected from any of the following: Nc-Spain 7 (CCAP deposit #2051/1; US 2010/0255577), NCTS-8 (U.S. Pat. No. 6,656,479) as an attenuated form of NC-1, Nc-Nowra (U.S. Pat. No. 7,361,359), or an attenuated mutant of any of strains CCAP deposit #2051/2 (Hipra Laboratories), BPA1, BPA2, BPA3, BPA4, BPA5, or BPA6 (U.S. Pat. No. 5,707,617), NC-1 (U.S. Pat. No. 6,787,146), or NE1 (equine isolate; ATCC deposit #209,622). The attenuated strain can also be a mutant in which a particular gene or genes has been modified such that the strain no longer expresses a particular protein or proteins, or functional equivalents of said protein(s). Said protein or proteins can include one or more of the following: phosphatidylthreonine synthase (PTS); microneme protein 1 (MIC-1); microneme protein 3 (MIC-3); immune mapped protein-1 (IMP-1); dense granule proteins 1, 6, or 7 (GRA1, GRA6, GRA7); apical membrane antigen (AMA1); surface antigen-1 or 4 (SAG1, SAG4); GRA2 (homolog of *Toxoplasma gondii* 28 kDa antigen); sortilin-like receptor; carbamoyl phosphate synthase II (CPS II); rhoptry neck protein (RON2); digalactolipid antigen; cyclophilin protein (CyP); NcP20 (US 2004/0131633); or dihydrofolate reductase (DHFR).

Methods for preparing immunogens derived from protozoa are known in the art. The protozoa can be attenuated or inactivated prior to use as an immunogen. Methods of attenuation and inactivation are well known to those skilled in the art. Methods for attenuation can include, but are not limited to, serial passage in cell culture, ultraviolet irradiation, and chemical mutagenesis. Methods of attenuation can also include targeted genetic manipulations, in which a particular gene, genes, or upstream or downstream regulatory regions, are disrupted or deleted. Such methods of genetic manipulation are well known to the skilled artisan.

Methods for inactivation include, but are not limited to, treatment with formalin, betapropriolactone (BPL) or binary ethyleneimine (BEI), or other methods known to those skilled in the art, such as sonication, treatment with peptidases, heat-shock, and freeze-shock. Inactivation by formalin can be performed by mixing the protozoa with 37% formaldehyde, to a final formaldehyde concentration of 0.05%. The protozoa-formaldehyde mixture is stirred constantly for approximately 24 hours at room temperature. The inactivated mixture is then tested for residual live protozoa by assaying for viability. Inactivation by BEI can be performed by mixing the protozoa suspension with 0.1 M BEI (2-bromo-ethylamine in 0.175 N NaOH), to a final BEI concentration of 1 mM. The protozoa-BEI mixture is stirred constantly for approximately 48 hours at room temperature, followed by the addition of 1.0 M sodium thiosulfate to a final concentration of 0.1 mM. Mixing is continued for an additional two hours. The inactivated mixture is then tested for residual live protozoa by assaying for viability.

Immunogenic compositions of the present invention can include one or more veterinarily-acceptable carriers. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, phthalic acid, Tris, trimethanmine hydrochloride, or phosphate buffers. Parenteral carriers can include sodium chloride solution, Ringer's dextrose, dextrose, trehalose, sucrose, lactated Ringer's, or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH, isotonicity, stability and other conventional characteristics, is within the skill of the art. See, e.g., texts such as Remington: The Science and Practice of Pharmacy, 20th ed, Lippincott Williams & Wilkins, pub., 2000; and The Handbook of Pharmaceutical Excipients, 4.sup.th edit., eds. R. C. Rowe et ai, APhA Publications, 2003. Veterinarily-acceptable carriers can also include any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

The immunogenic component can also include an adjuvant. Adjuvants include, but are not limited to, the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block co-polymer (CytRx; Atlanta, Ga.), SAF-M (Chiron; Emeryville, Calif.), AMPHIGEN® adjuvant, saponin, Quil A, QS-21 (Cambridge Biotech Inc.; Cambridge, Mass.), GPI-0100 (Galenica Pharmaceuticals, Inc.; Birmingham, Ala.) or other saponin fractions, monophosphoryl lipid A, Avridine lipid-amine adjuvant, heat-labile enterotoxin from *Escherichia coli* (recombinant or otherwise), cholera toxin, or pertussis toxin. A number of cytokines or lymphokines may be used as adjuvants, including the interleukins 1-α, 1-β, 2, 4, 5, 6, 7, 8, 10, 12 (see, e.g., U.S. Pat. No. 5,723,127), 13, 14, 15, 16, 17 and 18, the interferons-α, β and γ, granulocyte-macrophage colony stimulating factor (see, e.g., U.S. Pat. No. 5,078,996 and ATCC Accession Number 39900), macrophage colony stimulating factor, granulocyte colony stimulating factor, GSF, and the tumor necrosis factors α and β. Still other adjuvants include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Additional adjuvants include MPL™ (3-O-deacylated monophosphoryl lipid A; Corixa, Hamilton, Mont.). Also suitable for use as adjuvants are synthetic lipid A analogs or aminoalkyl glucosamine phosphate compounds (AGP), or derivatives or analogs thereof, which are available from Corixa (Hamilton, Mont.). Still other adjuvants include L121/squalene, D-lactide-polylactide/glycoside, pluronic polyols, muramyl dipeptide, killed *Bordetella*, saponins, such as Stimulon™ QS-21 (Antigenics, Framingham, Mass.), and particles generated therefrom such as ISCOMS (immunostimulating complexes).

For its use and administration into a subject, the freeze-dried immunogenic composition or vaccine composition can be reconstituted by rehydration with a solvent. The solvent is typically water, such as demineralized or distilled water, water-for-injection, but can also comprise physiological solutions or buffers, such as for example phosphate buffer solution (PBS).

The total content of components in a reconstituted ready-to-inject immunogenic composition or vaccine composition of the invention can be used to provide an injection at an isotonic concentration, e.g., within the range of about 100-1200 mOsm, generally within about 250-600 mOsm, and preferably about 330 mOsm.

Dosages of live microorganisms in an immunogenic compositions or vaccine composition, or in a reconstituted ready-to-inject immunogenic composition or vaccine composition, can range from about $10^2$ to about $10^7$ $CCID_{50}$/dose.

A reconstituted ready-to-use immunogenic composition or vaccine composition can be administered to an animal by injection through the parenteral or mucosal route, preferably intramuscular and subcutaneous. However, administration of such a reconstituted ready-to-use immunogenic composition or vaccine composition can also comprise intranasal, intravenous, intra-arterial, intraperitoneal, intrathecal, intraventricular, intraurethral, intrasternal, intracranial, epicutaneous, topical, or oral administration. The volume of a dose for injection can be from about 0.1 ml to about 2.0 ml, and preferably about 1.0 ml.

Stabilizers

The invention encompasses a method for freeze-drying protozoa, including intracellular protozoa from the Apicomplexa phylum, such as *Neospora caninum*. Prior to freeze-drying, the protozoa may be combined with, or resuspended in, at least one stabilizer. These stabilizers can preserve or assist in retention of the immunogenicity, infectivity, and viability of biological ingredients before, during, and after the freeze-drying process, whereby the biological ingredients can include, but not be limited to, protozoa, viruses, bacteria, fungi, proteins, polypeptides, among others. Stabilizers used in the present freeze-drying methods may have a beneficial aspect(s), including for example, uniform shape and color, and be safe for administration into a subject.

Stabilization of biological ingredients in dry form has typically involved the preservation of antitoxins, antigens and bacteria (Flosodort et al (1935) J. Immunol. 29, 389). However, a limitation in this process included partial denaturation of proteins when dried from an aqueous state at ambient temperatures. Drying from the frozen state helped reduce denaturation and led to better, although incomplete, preservation of biological ingredients, including bacteria and viruses (Stamp et al. (1947) J. Gen. Microbiol. 1, 251; Rightsel et al. (1967) Cryobiology 3, 423; Rowe et al. (1971) Cryobiology 8, 251).

A large number of compounds have been tested for their ability to stabilize different vaccines containing live-attenuated biological ingredients. Such compounds include SPGA (sucrose, phosphate, glutamate, and albumin; Bovarnick et al. (1950) J. Bacteriol. 59, 509-522; U.S. Pat. No. 4,000,256), bovine or human serum albumin, alkali metal salts of glutamic acid, aluminum salts, sucrose, gelatin, starch, lactose, sorbitol, Tris-EDTA, casein hydrolysate, sodium and potassium lactobionate, and monometallic or dimetallic alkali metal phosphate. Other compounds include, for example, SPG-NZ amine (e.g. U.S. Pat. No. 3,783,098) and polyvinylpyrrolidone (PVP) mixtures (e.g. U.S. Pat. No. 3,915,794).

The stabilizer may comprise at least one reducing monosaccharide, wherein the reducing monosaccharide may comprise glucose, galactose, fructose, mannose, sorbose, or combinations thereof.

The stabilizer may further comprise at least one non-reducing oligosaccharide, including trehalose, sucrose, raffinose, or combinations thereof.

Additional useful sugars include dextrose, glucose, lactose, and maltose.

The stabilizer may comprise at least one acid antioxidant compound, including aspartic acid, glutamic acid, ascorbic acid, or combinations thereof.

The stabilizer may comprise at least one sugar alcohol, including sorbitol, mannitol, xylitol, maltitol, or combinations thereof.

Some components, including stabilizers, may not be readily soluble. However, it is well within the reach of the skilled person to substitute suitably analogous components (e.g. by selecting a more soluble component), and/or to adapt the amounts or quantities of the insoluble component present in the stabilizer for the purpose of obtaining a soluble stabilizer. The solubility of a component can be easily checked by a visual solubility test. A solubility test comprises the steps of adding all of the components of the stabilizer at a temperature of about 55° C., and mixing for about 30 minutes. After approximately 24 hours at room temperature and without any agitation, the stabilizer can be visually checked for the appearance of precipitates. If the stabilizer is transparent or limpid, then all the components of the stabilizer are soluble.

Bulking Agents

Bulking agents are included in lyophilized protein formulations to increase product mass, adjust tonicity, improve product appearance, prevent product collapse, or aid in rehydration (Wang, Int. J Pharm., 203:1-60, 2000). Yet, bulking agents typically are believed to have little or no impact on the stability of the protein. While excipients, such as sucrose, are added specifically to increase protein stability (Carpenter et al., Pharm. Res., 14:969-75, 1997; and Carpenter et al., Eur. J Pharm., 45:231-8, 2002), the degree of damage to a protein during freeze-drying and subsequent storage is potentially affected by all the excipients in the formulation, including bulking agents.

The "T'g value" is defined as the glass transition temperature, which corresponds to the temperature below which the frozen matrix undergoes a structural transition from viscoelastic state to vitrous state, this transition is associated to drastic reduction of molecular mobility and hence reduction of degradation reactions. The bulking agent increases the T'g value of the immunogenic compositions and vaccine compositions, allowing the use of higher temperatures during freezing. One of the advantages of the inclusion of a bulking agent in the freeze-dried pastilles and cakes is that it allows for retention of the solid form of the pastilles without creating hydrogen bonds.

The bulking agent can be a pharmaceutically or veterinarily acceptable polymer such as, but not limited to, dextran, mannitol, maltodextrin, polyvinylpyrrolidone (PVP), crospovidone, and hydroxyethyl starch. Other starch derivatives include, but are not limited to, microcrystalline cellulose, methyl cellulose, carboxy methyl cellulose, hydroxypropylcellulose, hydroxyethyl methyl cellulose, and hydroxypropyl methyl cellulose. Advantageously, the bulking agent can be mannitol, dextran or PVP. Combinations of at least two bulking agents are also contemplated.

If dextran is used as a bulking agent, its molecular weight can be from about 5000 Da to about 70000 Da, preferably from about 10,000 Da to about 40,000 Da. If PVP is used as a bulking agent, its molecular weight can be from about 8,000 Da to about 360,000 Da, preferably from about 10,000 Da to about 60,000 Da. If maltodextrin is used as a bulking agent, its dextrose equivalent value (DE, which is a quantitative measure of the degree of starch polymer hydrolysis) can be from about 3 to about 20, preferably from about 5 to about 18, more preferably from about 10 to about 15. If hydroxyethyl starch is used as a bulking agent, its molecular weight can be from about 70,000 Da to about 450,000 Da, preferably from about 130,000 Da to about 200,000 Da. The degree of substitution of hydroxyethyl starch can be from about 0.4 to about 0.7, preferably from about 0.4 to about 0.6. The degree of substitution is defined as the number of hydroxyethyl group per glucose unit.

Lyophilization Process

The process of lyophilizing (freeze-drying) the immunogenic composition involves the steps of: (a) contacting the suspension or solution with the stabilizer, thereby forming a stabilized immunogenic suspension or solution; (b) cooling, at atmospheric pressure, the stabilized immunogenic suspension or solution to a temperature of less than about the T'g value of the stabilized immunogenic suspension; (c) drying the stabilized immunogenic suspension or solution by sublimation of ice at low pressure; and (d) removing excess residual water by further reducing pressure and increasing the temperature of the stabilized immunogenic suspension or solution.

The cooling step (b) can occur at temperatures of less than about −40° C. Drying the stabilized immunogenic suspensions or solution by sublimation of ice at low pressure (c) can occur at, for example, pressures lower than or equal to about 200 microbar, whereas a further reduction in pressure can occur at pressures lower than or equal to about 100 microbar. Finally, the temperature of the stabilized immunogenic suspension or solution during the removal of excess residual water (d) occurs at, for example, temperatures between about 20° C. and about 37° C. for biological products.

The moisture content of the freeze-dried material can range from about 0.5% to about 5% w/w, preferably from about 0.5% to about 3% w/w, and more preferably from about 1.0% to about 2.6% w/w.

Advantageously, the stabilized immunogenic suspension or solution comprising at least one bulking agent has a high T'g value of between about −36° C. to about −30° C., but can be lower than −36° C. and/or higher than −30° C., depending on the formulation composition and concentration. A high T'g value allows for higher temperatures during the water freezing step of the freezing process and/or the freeze-drying process, thereby decreasing exposure of the active immunogenic component to stress, avoiding substantial loss of activity. Therefore, it is critical to minimize these stresses as much as possible during the lyophilization process-for example, during the ice nucleation step.

In order to better control the pressure during the lyophilization process, an inert gas can be introduced into the chamber. One example of an inert gas would be nitrogen. However, nobel gases-ones that have extremely low reactivity with other substances-could also be used. Argon is an exemplary nobel gas that could be used. Air, however, because it contains 78% nitrogen, might also be used to control pressure during the lyophilization process.

Each step, including water freezing, and its removal during the primary and secondary desiccation stages, subjects the biological ingredients in the immunogenic suspensions or solutions of the invention to mechanical, physical and biochemical shock. These can have potentially adverse effects upon the structure, appearance, stability, immunogenicity, infectivity and viability of the biological ingredients.

The herein-disclosed stabilizers and lyophilization process can all be used for the preservation of any *Neospora caninum* isolate or immunogenic composition, or for any protozoan isolate or immunogenic composition. The immunogenic composition can comprise a live-attenuated microorganism, wherein the present process is the last step in the preparation of the vaccine. This process can also be used for the preservation of stock cultures of *N. caninum*, ensuring that maximum viability is maintained throughout storage. This process can also be an intermediate step in the process of preparing an inactivated immunogenic composition. The *N. caninum* isolate, or any other protozoan isolate, can be lyophilized using this process, and then later rehydrated and optionally combined with other rehydrated *N. caninum* preparations. It can then be inactivated by any of several means well known to those of skill in the art, and previously described herein.

The invention will now be further described by way of the following non-limiting Examples, given by way of illustration of various embodiments of the invention. They are not meant to limit the present invention in any fashion, however.

EXAMPLES

Example 1. Formulations and Lyophlisation Protocol

Following several rounds of testing, an optimal composition and concentration of the stabilizer solution was derived. The final formulation (Table 1) contained BSA, Tween 80, Trehalose, citric acid and EGCG (epigallocatechin gallate; an antioxidant). This formulation was DMSO-free, however, avoiding quality issues with the final freeze-dried pellet, as well as hazard issues (toxicity) for the operator and for the equipment (inflammability; explosion risk). Each of the reagents described in Table 1 can be varied as to its percent contribution, such as: BSA (5-25% w/v); trehalose (5-25% w/v); Tween® 80 (Croda Americas) (0.5-25% v/v); citric acid (1-10% w/v); and EGCG (0.1 to 5 mg/ML) or equivalent ascorbic acid (0.1 to 5 mg/ML). Generally speaking, if another sugar or sugar alcohol is substituted for trehalose, concentrations in the Table 1 stock should be 15-25%. The stabilizing solution shown in Table 1 includes a citric acid concentration of 2.5%, which is preferred. Concentrations of citric acid around 1.5% are also highly preferred. Other protein stabilizers can be used in replacement of bovine serum albumin, as is well known in the art, to include human serum albumin, for example at similar concentrations.

It should also be noted that many other sorbitan esters such as "Spans" ® (Croda Americas and Croda Europe Ltd) and their ethoxylates such as "Tweens"® (Croda) are useful in the practice of the invention to include (also at concentrations in the stabilizer solution of about 0.5-25% v/v), Span 20, 40, 60, 80 and 120 (monolaurate, monopalmitate, monostearate, monooleate, and isolsterate respectively) and Tween 20, 40 60 and 80 (monolaurate, monopalmitate, monostearate, monooleate PEG-20 sorbitans, respectively). In regard of Tween® and Span® concentrations that are useful, substantial effectiveness has been noted down to at least about 0.5% v/v final concentration. The stabilizer solution was stirred for 2 hours, and subsequently filtered through a 0.2 μm sterilizing filter.

TABLE 1

| Ingredient | BSA | Trehalose | Tween 80 | Citric Acid | EGCG | Water |
|---|---|---|---|---|---|---|
| Concentration | 15% (w/v) | 15% (w/v) | 12.5% (v/v) | 2.5% (w/v) | 0.45 mg/ml | 120 ml |

The *Neospora*-infected Vero cell culture was then harvested mechanically using a cell scraper. Since the infected cells are quite fragile, most of the parasites are released into the culture medium, which already contained some free parasite cells. Many of the recovered parasites are tachyzoites, although bradyzoite forms and oocysts can be noted. Marc-145 cells are an alternative culturing cell line. The concentration of protozoa in the harvested culture medium was determined by hemocytometer to be $9.09\times10^5$/ml.

In a representative example, the final formulation is assembled as follows. 45 ML of the harvested cell culture is mixed with 5 ML of FBS (fetal bovine serum) resulting in a solution that is now 10% FBS. 50 ML of this solution is mixed (1:1) with 50 ML of the above stabilizer solution, although the three components need not be mixed in this exact sequence. As noted above, the lyophilization and stabilization procedures of the present invention are generally applicable to all life cycle phases of Apicomplexa protozoans.

Two milliliters each of the final formulation was dispensed in 15 cc vials, partially stoppered, and loaded onto pre-cooled shelves, in preparation for lyophilization. A small amount of the mixture was used to determine the glass transition temperature, measured by differential scanning calorimetry (DSC). It should again be noted that ascorbic acid may be used as a replacement for EGCG, in the stabilizer solution at a concentration of 0.45 mg/ML or at any other concentration noted to be operable for EGCG (such as about 0.1 to about 5.0 mg/ML)

To minimize the detrimental effects on viability of the microorganism that can occur during the freezing stage of lyophilization, a modified protocol was developed, with the specific intent of better controlling the ice nucleation temperature during the freezing step. The drying chamber was pressurized up to 2 Bar, followed by rapid depressurization of the chamber to atmospheric pressure. The temperature within the chamber was then held at between $-1°$ C. and $-15°$ C. The temperature was then lowered to as low as $-50°$ C. during the primary drying period, and then subsequently raised to as high as $-35°$ C. This was below the glass transition temperature of the formulation, and prevented the freeze-dried pellet from collapsing and degrading. The temperature was then raised to 20° C. during the secondary drying step; residual moisture content of the freeze-dried product never exceeded 3%. During this protocol, gas was introduced into the chamber, to aid in better controlling the pressure as it is lowered.

The freeze-dried protozoa were then stored at $-70°$ C. After 37 days of storage, they were rehydrated with culture media. The concentration of viable protozoa immediately following rehydration was determined to be $7.0\times10^6$/ml, which equates to a 77% survival rate. The rehydrated protozoa were also used to infect a Vero cell culture. After 30 hours of incubation, the entire cell monolayer was infected, and within ~54 hours, the viable tachyzoites completed their life cycle within the host cells (data not shown). The protozoan culture was harvested after 54 hours, and viable microorganisms were counted via Trypan Blue staining and a hemocytometer; the concentration was determined to be $6.5\times10^6$ protozoa/mL. The method is applicable to corresponding life cycle stages of all the aforementioned additional protozoans.

Example 2. Effects of Stabilizer Concentration on Tachyzoite Viability

Utilizing the stabilizer solution of Table 1 at different concentrations, with or without fetal bovine serum (FBS) being present, the effect on viability of lyophilized *N. caninum* tachyzoites was assessed. Tachyzoites were lyophilized according to the protocol of Example 1, and following storage at $-80°$ C. for 37 days, were subsequently rehydrated in culture media. Viable tachyzoites were then enumerated using Trypan Blue staining and hemocytometer counting. The results (Table 3) show a correlation between the stabilizer concentration and the viability of lyophilized tachyzoites, where an increase in the concentration of stabilizer led to an increase in viability. A positive effect of including FBS in the stabilization buffer was also demonstrated, as the percentage of viable tachyzoites was higher when FBS was present than when it was not.

TABLE 2

| Experiment | 1 | 2 | 3 | 4 |
|---|---|---|---|---|
| % Stabilizer | 50 | 50 | 20 | 20 |
| Dilution Factor* | 2.2 | 2.0 | 1.375 | 1.25 |
| Serum (FBS) | Yes | No | Yes | No |
| Concentration prior to lyophilization (protozoa/ml) | $9.09 \times 10^5$ | $1.00 \times 10^6$ | $1.45 \times 10^6$ | $1.60 \times 10^6$ |
| Concentration following rehydration of lyophilized material (protozoa/ml) | $7.0 \times 10^5$ | $5.0 \times 10^5$ | $4.0 \times 10^5$ | $2.5 \times 10^5$ |
| % Viability | 77 | 50 | 27.6 | 15.6 |

*Dilution Factor = Total Solution volume/Antigen volume

The invention claimed is:

1. A method of lyophilizing a protozoan by controlling ice nucleation by pressurizing and depressurizing with an inert gas or air, wherein the method comprises the steps of:
   (A) Loading a mixture of cultured cells and a stabilizing buffer into a dryer chamber which is at approximately 5° C. and about 1 Bar, the cultured cells including protozoa infected cells;
   (B) Lowering the temperature of the chamber to between $-1°$ C. and $-15°$ C., and holding for approximately 5 minutes;
   (C) Pressurizing the chamber to between 1.2 to 2 Bar, and holding for approximately 45 minutes, while maintaining the temperature of the chamber at between $-1°$ C. and $-15°$ C.;

(D) Rapidly depressurizing the chamber to about 1 Bar, while holding the temperature at between −1° C. and −15° C.;
(E) Holding the pressure in the chamber at about 1 Bar, lowering the temperature to as low as −50° C., and holding for approximately 45 minutes;
(F) Holding the pressure in the chamber at about 1 Bar, the temperature at as low as −50° C., for a further approximate 90 minutes;
(G) Holding the temperature in the chamber at as low as −50° C., decreasing the chamber pressure to about 0.1 mBar, and holding for approximately 30 minutes;
(H) Holding the temperature in the chamber at as low as −50° C., decreasing the chamber pressure to about 0.01 mBar, and holding for approximately 60 minutes;
(I) Holding the pressure in the chamber at about 0.01 mBar, raising the temperature in the chamber to as high as −35° C., and holding for approximately 60 minutes;
(J) Holding the pressure in the chamber at about 0.01 mBar, and the temperature at as high as −35° C., and holding for up to an additional 3500 minutes;
(K) Decreasing the chamber pressure to about 0.005 mBar; raising the temperature to as high as 20° C., and holding for up to an additional 360 minutes;
(L) Holding the pressure in the chamber at about 0.005 mBar; and the temperature at as high as 20° C., for up to an additional 900 minutes.

2. The method of claim 1, wherein an inert gas is used for pressurizing and depressurizing of the chamber.

3. The method of claim 2, wherein the inert gas is nitrogen or argon.

4. The method of claim 1, wherein the method is the final step in the preparation of a vaccine.

5. The method of claim 1, wherein the method is an intermediate step in the preparation of a vaccine.

6. The method of claim 1 wherein the protozoa is from the phylum Apicomplexa.

7. The method of claim 6, wherein the protozoa is selected from the class Coccidia.

8. The method of claim 7, wherein the protozoa is selected from the order Eucoccidiorida.

9. The method of claim 8, wherein the protozoa is selected from the family Sarcocystidae.

10. The method of claim 9, wherein the protozoa is selected from the genus consisting of *Neospora*, *Hammondia*, and *Toxoplasma*.

11. The method of claim 10, wherein the protozoa is from the genus *Neospora*.

12. The method of claim 11, wherein the protozoa is *Neospora caninum*.

13. The method of claim 12, wherein the *Neospora caninum* is inactivated.

14. The method of claim 13, wherein the *Neospora caninum* is selected from the group consisting of: Nc-Spain 7, NCTS-8, Nc-Nowra, NC-1, and NE1.

15. The method of claim 12, wherein the *Neospora caninum* is live-attenuated.

16. The method of claim 15, wherein the live-attenuated *Neospora caninum* has a mutation in a protein selected from the group consisting of: PTS, MIC-1, MIC-3, IMP-1, GRA1, GRA6, GRA7, AMA1, SAG1, SAG4, GRA2, sortilin-like receptor, CPS II, RON2, digalactolipid antigen; CyP; NcP20, and DHFR.

17. The method of claim 15, wherein the *Neospora caninum* is selected from the group consisting of: Nc-Spain 7, NCTS-8, Nc-Nowra, NC-1, and NE1.

18. A composition comprising *Neospora caninum* lyophilized by the method of claim 1.

19. A *Neospora caninum* vaccine prepared by a process comprising the method of claim 1.

* * * * *